(12) United States Patent
Varga et al.

(10) Patent No.: US 7,951,913 B2
(45) Date of Patent: May 31, 2011

(54) METHOD OF POLYMYXIN B RECOVERY FROM FERMENTATION BROTH

(75) Inventors: Ivan Varga, Hlohovec (SK); Mária Bobálová, Banská Bystrica (SK); Eva Michalková, Banská Bystrica (SK); Mária Jakubcová, Banská Bystrica (SK)

(73) Assignee: Biotika A.S., Slovenska Lupca (SK)

( * ) Notice: Subject to any disclaimer, the term of this patent is extended or adjusted under 35 U.S.C. 154(b) by 0 days.

(21) Appl. No.: 12/303,205

(22) PCT Filed: May 11, 2007

(86) PCT No.: PCT/SK2007/050009
§ 371 (c)(1),
(2), (4) Date: Dec. 2, 2008

(87) PCT Pub. No.: WO2007/142611
PCT Pub. Date: Dec. 13, 2007

(65) Prior Publication Data
US 2009/0253894 A1    Oct. 8, 2009

(30) Foreign Application Priority Data
Jun. 2, 2006  (SK) .................................. 0083-2006

(51) Int. Cl.
*A61K 38/00* (2006.01)
(52) U.S. Cl. ........................................ 530/344; 530/319
(58) Field of Classification Search .................... None
See application file for complete search history.

(56) References Cited

U.S. PATENT DOCUMENTS

| | | | |
|---|---|---|---|
| 2,565,057 A * | 8/1951 | Ainsworth et al. | 424/118 |
| 2,571,104 A | 10/1951 | Benedict | |
| 2,595,605 A | 5/1952 | Petty | |
| 2,602,041 A | 7/1952 | Brown | |
| 2,964,406 A | 12/1960 | Strandskov et al. | |
| 3,094,460 A | 6/1963 | De Boer et al. | |
| 3,132,994 A | 5/1964 | Duffin et al. | |
| 3,281,331 A | 10/1966 | Bergkvist | |
| 3,317,404 A | 5/1967 | Prave et al. | |
| 3,318,867 A | 5/1967 | Jahnke | |
| 3,376,339 A | 4/1968 | Svanholm | |
| 3,413,398 A | 11/1968 | Weddle | |
| 3,494,832 A | 2/1970 | Florent et al. | |
| 3,679,742 A | 7/1972 | Umezawa et al. | |
| 3,687,810 A | 8/1972 | Kurihara et al. | |
| 3,929,571 A | 12/1975 | Kubota et al. | |
| 4,308,346 A | 12/1981 | Niwano | |
| 4,444,883 A | 4/1984 | Brown et al. | |
| RE32,455 E * | 7/1987 | Hamill et al. | 530/317 |
| 4,870,158 A | 9/1989 | Karol et al. | |
| 4,912,036 A | 3/1990 | Cichanowicz et al. | |
| 5,147,441 A | 9/1992 | Megeed et al. | |
| 5,510,242 A | 4/1996 | Blais et al. | |
| 5,894,018 A | 4/1999 | Davila et al. | |
| 5,929,299 A | 7/1999 | Ikeda et al. | |
| 5,952,313 A | 9/1999 | Carlson | |
| 6,368,847 B1 | 4/2002 | Line et al. | |
| 6,579,696 B1 | 6/2003 | Shekhani et al. | |
| 6,719,973 B1 | 4/2004 | Ding et al. | |
| 7,070,992 B2 | 7/2006 | Baum et al. | |
| 7,297,551 B2 | 11/2007 | Ding et al. | |
| 2003/0008355 A1 | 1/2003 | Harrison | |

FOREIGN PATENT DOCUMENTS

| | | |
|---|---|---|
| CN | 1120585 | 4/1996 |
| CN | 1384200 | 12/2002 |
| CN | 1583171 | 2/2005 |
| DE | 4227682 | 10/1993 |
| EP | 0173937 | 3/1986 |
| EP | 0173944 | 3/1986 |
| EP | 0265127 | 4/1988 |
| EP | 0328256 | 8/1989 |
| EP | 1529784 | 5/2005 |
| FR | 1096978 | 6/1955 |
| GB | 742589 | 12/1955 |
| GB | 755370 | 8/1956 |
| GB | 757246 | 9/1956 |
| GB | 782926 | 9/1957 |
| GB | 874188 | 8/1961 |
| GB | 974334 | 11/1964 |
| GB | 991602 | 5/1965 |
| GB | 1064300 | 4/1967 |
| GB | 1119668 | 7/1968 |
| GB | 2154606 | 9/1985 |
| JP | 53053680 | 5/1978 |
| JP | 53095991 | 8/1978 |
| JP | 54128501 | 10/1979 |
| JP | 55081584 | 6/1980 |
| JP | 60184100 | 9/1985 |
| JP | 60199398 | 10/1985 |
| JP | 63180860 | 7/1988 |

(Continued)

*Primary Examiner* — Nashaat T Nashed
(74) *Attorney, Agent, or Firm* — Michael Best & Friedrich LLP

(57) ABSTRACT

The invention is related to the method of polymyxine B recovery from fermentation broth for the purpose of pure substance recovery. The invention mentioned above is obtained by using the method of polymyxine B recovery from fermentation broth according invention, which abstract is characterized by, that the filtrate is obtained from fermentation broth, its pH and color is adjusted and purified on non-ionogenic synthetic adsorbents of polystyrene type with specific surface 500 till 1000 $m^2 \cdot g^{-1}$ and fabric size 3 till 30 nm. The polymyxine B is eluated from adsorbent by aqueous solution of organic solvent. The polymyxine B base is coagulated from eluate after adjustment of pH to alcaline area. The polymyxine B base is converted by mineral acid to polymyxine B salt solution, from which is obtained crystal substance by drying.

6 Claims, No Drawings

FOREIGN PATENT DOCUMENTS

| | | |
|---|---|---|
| JP | 1296998 | 11/1989 |
| JP | 4009304 | 1/1992 |
| JP | 4071478 | 3/1992 |
| JP | 4200388 | 7/1992 |
| JP | 8098678 | 4/1996 |
| JP | 8126495 | 5/1996 |
| JP | 9121884 | 5/1997 |
| JP | 2003259861 | 9/2003 |
| KR | 920008386 | 9/1992 |
| MD | 2078 | 1/2003 |
| MD | 2285 | 10/2003 |
| RU | 2113471 | 6/1998 |
| RU | 2113472 | 6/1998 |
| RU | 2115721 | 7/1998 |
| RU | 2132880 | 7/1999 |
| RU | 2139348 | 10/1999 |
| RU | 2158758 | 11/2000 |
| RU | 2203317 | 4/2003 |
| RU | 2213779 | 10/2003 |
| RU | 2214453 | 10/2003 |
| RU | 2218395 | 12/2003 |
| RU | 2223313 | 2/2004 |
| RU | 2223499 | 2/2004 |
| RU | 2225441 | 3/2004 |
| WO | 01/27628 | 4/2001 |

* cited by examiner

METHOD OF POLYMYXIN B RECOVERY FROM FERMENTATION BROTH

This application is a U.S. national phase application filing of International Patent Application No. PCT/SK2007/0050009, filed 11 May 2007, which claims priority to Slovak Patent Application No. PP 0083-2006, filed 2 Jun. 2006. The entire contents of each of the foregoing applications are incorporated herein by reference.

TECHNICAL FIELD

The invention is related to method of polymyxin B recovery from fermentation broth.

BACKGROUND ART

Polymyxin is a complex of very similar polypeptide antibiotics isolated from different types of *Bacillus polymyxa* strains and related species. It is a cyclic polypeptide with free amino acid groups containing characteristic constituents such as α,γ-aminobutanic acid, L-treonine and fatty acids (6-methyloktanoyl acid, 3-hydroxy-6-methyloktanoyl acid, 6-methylheptanoyl acid, heptanoyl acid, oktanoyl acid, nonanoyl acid). This complex was divided by semi-preparative PLRP-S with reverse phase on 7 components (Orwa J. A., Govaert C., Busson R., et all, 2001, J. Chromatography A, 912, 369-373). The structure was characterized by $^1$H- and $^{13}$C-NMR methods and molecular weight was measured by mass spectroscopy method. It confirmed the structure of polymyxin $B_1$, Ile-$B_1$, $B_2$, $B_3$ and $B_4$. The further two components, polymyxin $B_5$ and $B_6$, were isolated for the first time and characterized at this study.

Polymyxin B and E have lower toxicity like another polymyxin and they are preferred for medical use, mainly antibacterial more effective polymyxin B.

The procedures for recovery of polymyxin from fermentation broth in principal are based on application of activated carbon and ion-exchange. U.S. Pat. No. 2,565,057, describes a character of polypeptide antibiotic base as a metabolic products of *Bacillus aerosporus* and *Bacillus polymyxa*; there are listed also methods of its recovery from culture media by using adsorption properties of activated carbon. The first part of impurities are separated from the filtrate of the broth by activated carbon in acid conditions (pH 2.5). The discolored solution of antibiotic is adjusted to neutral pH and then it is adsorbed onto active carbon. The adsorbed antibiotic is eluted by aqueous solution of acid acetone. The eluate is purified by adjustment of pH, separation of acetone and re-adsorption on activated carbon, neutralization of the eluate with $CaCO_3$ and finalization by lyophilization of the antibiotic solution. Another alternative of antibiotic purification from eluate is preparation of insoluble salts such as precipitation by picric acid and reconversion of this salt into aqueous soluble salts usually in a form of sulphates (M. Harold et al.: Antibiotika CsAV Praha, 1957, page 285-288).

In a further two patents (GB 742 589 and GB 782 926) the filtrates from the fermentation broth are purified in weak acid ion-exchangers in different column systems. The adsorbed polymyxin is eluted by a solution of mineral acid or buffer solution with a pH in a range from 3 to 5. The obtained eluate is purified on an anion exchanger or using a strong acid cation exchanger. This repurified eluate is concentrated and polymyxin is precipitated by addition of alkaline solution. Precipitation occurs in a range of temperature from 60° C. to 90° C.

U.S. Pat. No. 3,132,994 (1964) describes the method of increased purification of crude sulphates- and N-methylsulphonates of polymyxin B and E. The background of this method is oxidation of these salts solutions in acid or neutral pH (pH 3.5 till 7.5) with 1% water solution of $KMnO_4$. In the next step the low molecular weight materials are separated, including Mn-cations in a strong acid cation exchanger in $H^+$ cycle, where the polymyxin is not adsorbed.

The procedure for recovery and purification of amphoteric and alkaline antibiotics including polymyxin B, using reactive extraction into organic solvent limited with aqueous mixture and extraction in a present of carriers di-(2-ethylhexyl)-ester or dinonyl ester of phosphoric acid is described in patent GB 979 887 (1964). Polymyxin B is extracted from the broth into 1% solution of di-(2-ethylhexyl)-ester of phosphoric acid in buthylacetate at pH 7. Purification of polymyxins B and E from acid solutions by alkaline reagent in a present of chelating agents to form complexes of cations Ca, Mg, Mn, Fe is describe in patents GB 1089765 (1964) and U.S. Pat. No. 3,413,398. The antibiotic are precipitate in a form of base solution by using alkaline agents such as hydroxides and carbonates of alkaline metals and ammonium hydroxide at pH 8.5 till 11 and addition of chelating agents avoid coprecipitation of impurities. There is described a list of chelating agents, which were added in equivalent ratio as the polyvalent inorganic ions present. The precipitation of antibiotic base may occur in 10% water solution of acetone. In the examples of these patents are described methods for purification of polymyxin B, where the acid solution of crude polymyxin B is oxidized with $KMnO_4$, according to the patent GB 991602. The leftover $KMnO_4$ is eliminated by $H_2O_2$. This is continued further with precipitation of base in presence of ethylenediamine-N,N,N,N' tetraacetic acid tetra sodium salt. The base is filtered off, washed and vacuum-dried. The base is converted to the sulphate of polymyxin B by molar equivalent of $H_2SO_4$. In described procedures of recovery of polymyxin B solid substance from broth, the broth is purified by complicated methods and crude antibiotic is obtained. The crude antibiotic must be purified in several steps to get a pure substance.

DISCLOSURE OF THE INVENTION

Listed disadvantages are eliminated by the method of polymyxin B recovery from fermentation broth according to the invention, a summary of which is that the filtrate of the fermentation broth is purified on non-ionogenic synthetic adsorbents of polystyrene types, polymyxin B is eluted from the adsorbent by aqueous solution of organic solvent, the base of polymyxin B is precipitated from eluate, then it is converted by mineral acid to a mineral salt of polymyxin B, from which is obtained a crystal substance by drying.

The biomass and insoluble components of culture media are separated. The obtained filtrate is adjusted to a value pH from 2 to 6 and eventually discolored by activated carbon in amount 1 till 5 g per 1 $dm^3$ of filtrate before the next treatment. Discolored or un-discolored filtrate at a pH 2 till 6, preferably pH 2.5 till 3.5, is purified on non-ionogenic synthetic polystyrene adsorbents with a specific surface 500 till 1000 $m^2 \cdot g^{-1}$ and fiber size 3 to 30 nm.

The adsorbed polymyxin B is eluted with non-acid or acid aqueous solution of organic solvent with a concentration 20 to 60% at a pH 2 till 4, particularly with lower alcohol or ketone, preferably with methanol, ethanol, propanol, secondary propanol and acetone.

From obtained water-organic eluate, or from eluate after partial or total separation of organic solvent, polymyxin B base is precipitated by addition of water solution of mineral alkaline agent, preferably NaOH, KOH, NH$_4$OH at a pH 8 till 12, preferably at a pH 9 till 11. The base is precipitated at a temperature 20 till 60° C. The precipitated polymyxin B base is filtered off and washed by deionized water at temperature 30 till 80° C. Into washed polymyxin B base, eventually into water suspension of base, a solution of mineral acid is added, such as HCl, H$_2$SO$_4$, to a value pH 5 till 7.5. The obtained solution of polymyxin B is eventually discolored by activated carbon in amount 0.1 till 0.5 g per g of polymyxin B and the pure solution of substance is dried.

The invention is supplemented by examples, which do not limit its scope.

EXAMPLES OF EMBODIMENTS

Example 1

The biomass was separated by centrifugation from 2.1 dm$^3$ of fermentation broth with 3.1 g of polymyxin B. The supernatant was acidified with 10% solution of H$_2$SO$_4$ to pH 3, activated carbon was added in amount 4 g and after 30 minutes suspension was filtered out. Discolored clear filtrate was percolated through column fulfilled with 500 ml of non-ionogenic adsorbent DIAION® HP 21, with flow rate 2 dm$^3$·h$^{-1}$. The column was washed after adsorption by 500 ml of deionized water. The adsorbed polymyxin B was eluted with 40% aqueous solution of acetone under flow rate 0.5 dm$^3$·h$^{-1}$. It was obtained 0.84 dm$^3$ of eluate with amount 2.2 g of polymyxin B. Into the eluate was added under very slow agitation at laboratory temperature, 20% aqueous solution of NaOH to a value pH 11. After 2 h of crystallization the polymyxin B base was filtered off and washed with 2 dm$^3$ of deionized hot water at the a temperature of 70° C. It was obtained 20 g of moist product of polymyxin B base, which was mixed together with 5 ml of deionized water, and 10% solution of H$_2$SO$_4$ was slowly added till polymyxin B sulphate formed. Into 50 ml of polymyxin sulphate solution at a pH 6 was added 0.5 g of activated carbon and after 45 min, the suspension was filtered off. The discolored solution was then filtered through the membrane with fiber size 0.45 μm and 0.22 μm. The product was recovered by freeze-drying. It was obtained 1.7 g of polymyxin B sulphate with purity 7900 I.U./mg.

Example 2

From the eluate which was prepared according to example 1, acetone was separated by vacuum distillation. It was obtained 0.5 dm$^3$ of concentrate, which was adjusted to pH 7.5 with concentrated NH$_4$OH at the a temperature of 60° C. and then was added 20% solution of NaOH to a final pH of 12. After 2 hours of crystallization at a temperature of 40° C. polymyxin base was obtained, which was filtered off and washed 5 times with 0.3 dm$^3$ of deionized water at a temperature of 30° C. It was obtained 15 g of moist precipitate, which was recovered according to example 1. It was obtained 1.3 g of polymyxin B sulphate with purity 8100 I.U./mg.

Example 3

The procedure according to example 1 was followed with the following difference that 60% ethanol was used for elution. It was obtained 0.58 dm$^3$ of eluate, which was recovered according to example 1 with the difference that polymyxin base was precipitated by NH$_4$OH to a pH of 8. It was obtained 1.2 g of polymyxin B sulphate with purity 7200 I.U./mg.

Example 4

The biomass and insoluble parts were filtered off by vacuum filtration from 2.1 dm$^3$ of fermentation broth with amount of polymyxin B being 2.8 g. The filtrate was adjusted by NaOH at a pH 6 and it was adsorbed to column filled with adsorbent SEPABEADS® SP 207 (brominated styrene-divinylbenzene).

After washing of the column with deionized water the antibiotics were eluated with 20% solution of ethanol acidified with H$_2$SO$_4$ to a value pH 2.5. Into 1.2 dm$^3$ of eluate was added under mixing 20% aqueous solution of KOH to a value pH 8. The polymyxin base which was filtered off was washed 3 times with 0.1 dm$^3$ of deionized water at the temperature of 30° C. To the 12 g of moist polymyxin B base, 10% solution of H$_2$SO$_4$ was added under stirring very slowly to a pH of 5 to form polymyxin B sulphate. 40 ml of polymyxin B sulphate solution was discolored by 0.7 g of active carbon, filtered off through a 0.22 μm membrane and lyophilized. It was obtained 1.25 g of polymyxin B sulphate with purity 7600 I.U./mg Example 5

From 4 dm$^3$ of fermentation broth containing 4.4 g of polymyxin B at pH 6 was obtained by micro filtration 4.2 dm$^3$ of clear permeate, which was acidified by H$_2$SO$_4$ to pH 3. Into the solution was added 21 g of activated carbon and after 1 hour of mixing, the suspension was filtered off. Discolored permeate was percolated through a column filled with 1.2 dm$^3$ of non-ionogenic adsorbent AMBERLITE® XAD-4 (macroreticular crosslinked styrene-divinylbenzene polymer). After washing of column with deionized water the polymyxin B was by eluted with 60% aqueous solution of secondary propanol. It was obtained 1.2 dm$^3$ of eluate, which was adjusted to pH 10.8 with a solution of NaOH. The base which formed was separated by centrifugation and washed with hot deionized water, the pH of washed water being 7.8. It was obtained 25 g of moist base which was mixed together with 10 ml of deionized water. A solution of 10% H$_2$SO$_4$ was slowly added till polymyxin B sulphate solution was formed at pH 7. The solution of polymyxin B sulphate (70 ml) was discolored with 0.3 g of active carbon, filtered through a 0.22 μm membrane and lyophilized. It was obtained 2.4 g of polymyxin B sulphate with purity 7700 I.U./mg.

INDUSTRIAL APPLICABILITY

The method of polymyxin B recovery according to invention may be used for recovery of pure antibiotic from fermentation broth.

The invention claimed is:
1. A method of polymyxin B recovery from fermentation broth comprising:
  (a) contacting clarified fermentation broth at a pH of 2 to 3.5 with a non-ionogenic synthetic polystyrene adsorbent or derivative thereof with a specific surface of 500 to 1000 m$^2$·g$^{-1}$ and a pore radius of 3 to 30 nm;
  (b) eluting polymyxin B from the adsorbent with an aqueous solution of an organic solvent to form an eluate;
  (c) precipitating the polymyxin B from the eluate;
  (d) adding mineral acids to the precipitate to form polymyxin B solution; and
  (e) drying the polymyxin B solution to form a crystalline substance.
2. The method according to claim 1, wherein the aqueous solution of organic solvent of step (b) comprises a ketone, or methanol, ethanol, propanol, or secondary propanol, or combinations thereof, at a concentration of 20 to 60% by weight.

3. The method according to claim 1 wherein mineral acid is added in step (d) until the pH of solution is from 5 to 7.5.

4. The method of claim 1, wherein the clarified fermentation broth is discolored using activated carbon in amount of 1 to 5 g per 1 dm$^3$ of filtrate.

5. The method of claim 2, wherein the organic solvent comprises acetone.

6. A method of polymyxin B recovery from fermentation broth comprising:
  (a) contacting clarified fermentation broth at a pH of 2 to 3.5 with a non-ionogenic synthetic polystyrene adsorbent or derivative thereof with a specific surface area of 500 to 1000 m$^2 \cdot$g$^{-1}$ and a pore radius of 3 to 30 nm;
  (b) eluting polymyxin B from the adsorbent with an aqueous solution of organic solvent to form an eluate;
  (c) adjusting the pH of the eluate to 8 to 12 at a temperature of 20 to 60° C., thereby precipitating the polymyxin B from the eluate;
  (d) adding mineral acids to the precipitate to form polymyxin B solution; and
  (e) drying the polymyxin B solution to form a crystalline substance.

* * * * *